United States Patent [19]
Gilbert et al.

[11] 4,350,292
[45] Sep. 21, 1982

[54] CENTRIFUGAL FEEDER

[75] Inventors: Ian D. Gilbert, St. Albans, England; Michael T. Halloran, Pembroke Pines; Ermi Roos, Hialeah, both of Fla.

[73] Assignee: Coulter Electronics, Inc., Hialeah, Fla.

[21] Appl. No.: 107,704

[22] Filed: Dec. 27, 1979

[51] Int. Cl.³ .............................................. B05B 17/04
[52] U.S. Cl. ....................................... 239/7; 239/223; 239/681
[58] Field of Search ................... 239/7, 681, 684, 223, 239/224, 214 W, 214, 677, 653; 414/301, 206

[56] References Cited

U.S. PATENT DOCUMENTS

| | | | |
|---|---|---|---|
| 41,321 | 1/1864 | Rogers | 239/653 |
| 3,220,740 | 11/1965 | Kavan et al. | 239/677 |
| 3,281,076 | 10/1966 | Burnside et al. | 239/7 |
| 3,536,043 | 10/1970 | Eppe | 239/224 X |
| 3,679,098 | 7/1972 | Weiss | 239/677 X |
| 3,823,409 | 7/1974 | Carrell | 239/7 X |

FOREIGN PATENT DOCUMENTS 2546324  4/1977  Fed. Rep. of Germany ...... 239/681

*Primary Examiner*—Andres Kashnikow
*Assistant Examiner*—Paul A. Sobel
*Attorney, Agent, or Firm*—Silverman, Cass & Singer, Ltd.

[57] ABSTRACT

A centrifugal feeder includes a cylindrical feeder disc having an upwardly inclined uniform surface which is designed to expel particles placed thereon in a predetermined fashion by centrifugal force. The upwardly inclined surface of the disc may be designed to have a first predetermined expulsion rate which is the initial speed at which the disc must be rotated to expel any of the particles from the surface thereof. The disc also may be designed to have a final expulsion rate at which all particles placed on the surface thereof are expelled. The disc is rotated at a controlled rate of speed and at a controlled rate of change of speed to expel the particles in the manner desired in a linear or non linear fashion. The feed or expulsion rate of the particles is determined by the design of the disc and the rotation speed of the disc and essentially is independent of the size and density of the particles and the viscosity of the surrounding fluid in which the disc is rotated.

19 Claims, 4 Drawing Figures

CENTRIFUGAL FEEDER

BACKGROUND OF THE INVENTION

The invention relates to a centrifugal feeder for feeding particles and more particularly to a feeder including a feeder disc having a surface from which the particles may be expelled at a predetermined rate and at predetermined rotational speeds.

In studying industrial particles it is desirable to separate the particles so that each particle independently may be examined. The particles may be examined to count the particles, to determine the size of the particles in a particular particulate sample and for other characteristics. Therefore, it is desirable to have a convenient method to feed the particles one at a time into the examining or sensing zone in particle study devices. While it may not be possible to guarantee physical separation of each particle from one another, it would be desirable to feed the particles at a sufficiently uniform rate to provide statistically significant separation.

One such particle study device in which the particles are to be studied is shown and described in U.S. Pat. No. 4,140,966. The particles are fed into the particle sensing zone in this device by an auger type device. Particles which are fed to the apparatus disclosed in said patent by the auger may not all be separated one from each other until they move down the director bore thereof toward the sensing zone as described in the patent. Further, the auger may separate particles of one size range much better than those in other size ranges.

SUMMARY OF THE INVENTION

The above and other disadvantages of prior art feeding devices and techniques are overcome in accordance with the present invention by providing a centrifugal feeder disc which is rotated at a predetermined rate to expel the particles from the surface thereof in a predetermined manner. The feeder disc surface is upwardly inclined and may be designed to have an initial particle discharge rate and a final particle discharge rate and a rate of rotation which is controlled between the initial and final rate to discharge the particles in the desired manner.

DESCRIPTION OF THE PREFERRED EMBODIMENTS

Figure 1:
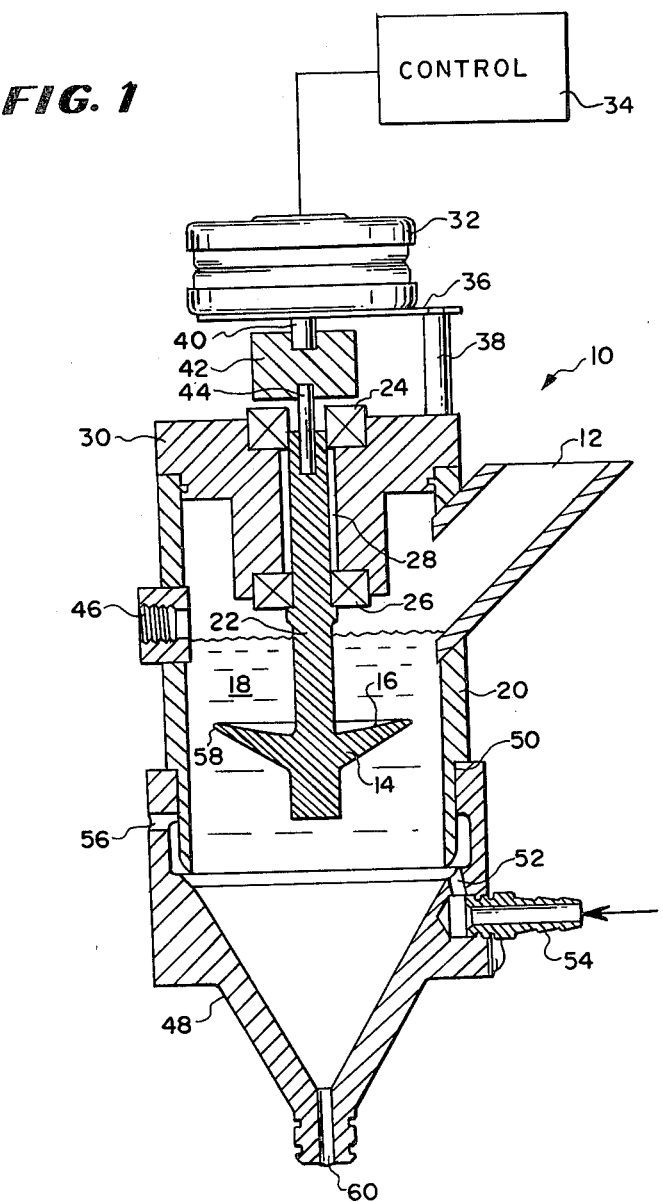
FIG. 1 is a sectional side view of the centrifugal feeder.

As indicated above, the invention is concerned with a centrifugal feeder for expelling particles at predetermined rates and speeds. Referring now to FIG. 1, the centrifugal feeder of the invention is designated generally at 10. The particles or particulate matter to be fed or expelled (not shown) may be loaded into the feeder 10 through a sample slot or port 12 and placed on a feeder or rotor disc 14. The particles will be placed on an upper surface 16 of the disc 14 when the disc is not rotating or when the disc is rotating slowly.

The disc 14 may be immersed in a fluid 18, such as an electrolyte, or may be above the fluid surface or could be utilized without a fluid. The slot or port 12 is mounted or molded into an upstanding body wall 20 preferably cylindrical, which surrounds the rotor disc 14 and contains the fluid 18. The rotor disc 14 may be formed integrally with or may be affixed to a drive shaft 22 which is rotated in a pair of upper and lower bearings 24 and 26. The bearings 24 and 26 and shaft 22 are mounted in a passageway 28 formed in an upper mounting member 30 which may be engaged into the upper end of the body member 20. The shaft 22 and rotor disc 14 are rotated by a motor 32 controlled by a control 34. The motor 32 may be a stepper motor or may be an electrical DC motor or other type of motor providing the functions hereinafter described.

The motor 32 is mounted onto the mounting member 30 by a motor mounting plate 36 supported by a plurality of pins or posts 38. The motor 32 includes a drive shaft 40 which is affixed to a flexible coupling 42. The flexible coupling 42, of any conventional type, isolates the motor vibrations from the drive shaft 22 and hence the disc 14 and is affixed to the drive shaft by a pin 44. The fluid 18 has an uppermost level maintained by an overflow port 46 mounted in one portion of the body wall 20. A fluid coupling and discharge member 48 is sealingly secured to a bottom flange 50 of the body wall 20. The coupling member 48 includes a fluid entrance port 52 which may include a fitting 54 engaged therein which may be coupled to a suitable fluid supply by a line (not shown). The fluid or electrolyte flows into the port 52 to flush the inside of the body wall 20 and may exit through the overflow port 46 or through a drain port 56.

In operation, as the particles are rotated on the rotor 14 the particles will move by centrifugal force up the surface 16 to an outer rim 58 of the rotor disc 14. As the particles are expelled from the rotor 14 by centrifugal force at the desired rate, they fall away from the rotor 14 and pass downwardly through an exit port 60 with the electrolyte fluid, if any. The port 60 will be connected to the sensing zone of a particle study device (not shown).

Figure 2:
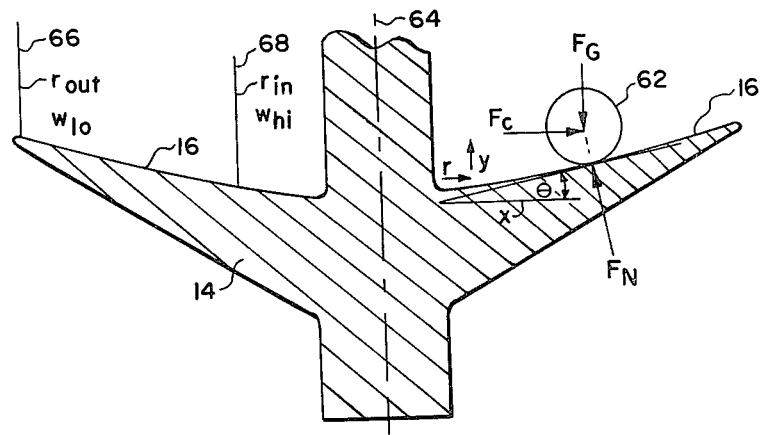
FIG. 2 is an enlarged sectional side view of a feeder disc of the centrifugal feeder.

Referring now to FIG. 2, an enlarged view of the feeder disc 14 is illustrated with one greatly enlarged particle 62 resting on the upper surface 16 of the disc 14. The particle 62 illustrated for explanation, would in operation, be one of a numerous number of particles loaded onto the surface 16 which would be of various sizes, but generally would be of a size many times smaller than the illustrated particle 62. The size of particle 62 is utilized to illustrate the forces acting thereon on the surface 16 as the feeder disc 14 is rotated. The disc 14 is rotated about an axis 64 which generally is an axis perpendicular to the horizontal plane.

The disc surface 16 is generally of a conical shape with the concave side uppermost and symmetrical about the axis 64. Utilizing a simplified case, where the particles of interest 62 are generally spherical and roll without slipping, it is possible to design the shape of the surface 16 such that at a given rate of rotational speed, stability exists between the gravitional and centrifugal forces. With the proper surface shape, stability will not exist outboard of an equilibrium radius at a given speed, so that particles lying outboard of the equilibrium radius (at a greater radius) are thrown off and particles lying inboard (closer to the axis 64) either remain stationary, roll toward the axis 64 or roll toward the equilibrium radius. For a single particle in this quasi-equilibrium state (which really is being accelerated in a centrifugal sense) forces acting on the particle 62 are as follows:

$$F_G = mg \tag{1}$$

$$F_C = m\omega^2 r \tag{2}$$

The gravitational force $F_G$ and the centrifugal force $F_C$ are shown by arrows in FIG. 2. The resultant force $F_N$ normal to the tangent of the particle 62 also is shown by an arrow. For quasi-equilibrium to exist for the particle 62, $F_N$ must equal the vector sum of $F_C$ plus $F_G$ or:

$$\frac{F_C}{F_G} = \tan\theta = \frac{dy}{dr} \tag{3}$$

In this equation, the angle theta ($\theta$) is the angle between the horizontal plane and a line tangent with the surface 16 at the point of contact with the particle 62. The radius increasing from the axis 64 is shown by the arrow "r". The arrow "y" represents the distance from a horizontal plane "x" parallel with the axis 64 for each radius of the surface 16. Substituting the values for $F_C$ and $F_G$ in equation (3) results in:

$$\frac{dy}{dr} = \frac{F_C}{F_G} = \frac{m\omega^2 r}{mg} = \frac{\omega^2 r}{g} \tag{4}$$

Taking the integral of the formula (3) and substituting in equation (4) results in:

$$\int \frac{dy}{dr} dr = \int \frac{\omega^2 r}{g} dr = \frac{\omega^2}{g} \int r\, dr = \tag{5}$$

$$\frac{\omega^2}{g} \frac{r^2}{2} + k = y(r) \tag{6}$$

Any point radially outward from the axis 64 on the surface 16 must satisfy equation (6). Equation (6) is not particularly useful for designing the surface profile 16 of the disc 14, so it is preferable to rewrite the formula to provide a more useable version.

Assume it is desirable to design the surface 16 so that the feeder 10 will expel a linear volume of particles per unit of angular acceleration (a linear ramp or increase in the rotational speed of the rotor 14 will produce a feed rate uniform with time). Further, to aid in the assumption it will be assumed that the surface 16 is covered initially with a uniform layer of particles of thickness (t) and it will be assumed that (dy/dr) is small.

In this derivation, a line 66 shown in FIG. 2 is representative of a radius on the surface 16 which is equal to $r_{out}$ (radius outside) and $\omega_{lo}$ (omega low) and a line 68 is indicative of $r_{in}$ (radius inside) and $\omega_{hi}$ (omega high). The time derivative of the particle volume is equal to a constant $c_1$ which is equal to the time derivative of omega times a constant $c_2$:

$$\dot{V} = c_1 = c_2 \dot{\omega} \tag{7}$$

The total volume ($V_{tot}$) shown in formula (8) is the volume inside ($V_{in}$) of the equilibrium radius plus the volume outside ($V_{out}$) of the equilibrium radius with the equilibrium radius being some radius on the surface 16.

$$V_{tot} = V_{in} + V_{out} \tag{8}$$

$$V_{out} = V_{tot} - V_{in}$$

The volume between any two radii is equal to:

$$V = \pi t \cdot (r_1^2 - r_2^2) \tag{9}$$

Substituting equation (9) into equation (8) and solving for r results in:

$$V_{out} = \pi t \cdot (r_{out}^2 - r_{in}^2) - \pi t \cdot (r^2 - r_{in}^2) \tag{10}$$

$$= \pi t \cdot (r_{out}^2 - r^2)$$

$$V_{out} = V(r) = \pi t r_{out}^2 - \pi t r^2$$

$$\pi t r^2 = \pi t r_{out}^2 - V(r)$$

$$r^2 = \frac{\pi t r_{out}^2 - V(r)}{\pi t}$$

$$r^2 = r_{out}^2 - \frac{V(r)}{\pi t}$$

$$r = \left(r_{out}^2 - \frac{V(r)}{\pi t}\right)^{\frac{1}{2}}$$

The volume discharged before reaching any given rotational speed ($\omega$) may then be found:

$$V(\omega) = V = \int_{\omega_{lo}}^{\omega} c = c \cdot (\omega - \omega_{lo}) = c\omega - c\omega_{lo} \tag{11}$$

$$\omega = \frac{V}{c} + \omega_{lo}$$

$$\omega^2 = \frac{V^2}{c^2} + \frac{2V}{c}\omega_{lo} + \omega_{lo}^2$$

Substituting the equations derived in (10) and (11) in the formula previously derived for y(r) in equation (5):

$$y(r) = \frac{1}{g} \int \left(\frac{V^2}{c^2} + \frac{2V}{c}\omega_{lo} + \omega_{lo}^2\right) \left(r_{out}^2 - \frac{V}{\pi t}\right)^{\frac{1}{2}} dr \tag{12}$$

Substituting in formula (12) the value for V found in formula (9) results in the formula:

$$y(r) = \frac{1}{g} \int \left(\frac{V^2}{c^2} + \frac{2V}{c}\omega_{lo} + \omega_{lo}^2\right) \cdot \tag{13}$$

$$\left(r_{out}^2 - \frac{\pi t}{\pi t} r_{out}^2 + \frac{\pi t}{\pi t} r^2\right)^{\frac{1}{2}} dr$$

$$= \frac{1}{g} \int \left(\frac{V^2}{c^2} + \frac{2V}{c}\omega_{lo} + \omega_{lo}^2\right) r\, dr$$

$$y(r) = \frac{1}{g} \int \frac{V^2 r}{c^2} + \frac{2Vr}{c}\omega_{lo} + \omega_{lo}^2 r\, dr$$

Squaring the value for V in formula (10) results in the formula:

$$V^2 = \pi^2 t^2 (r_{out}^2 - r^2)(r_{out}^2 - r^2) \tag{14}$$

$$V^2 = \pi^2 t^2 (r_{out}^4 - 2r^2 r_{out}^2 + r^4)$$

The value of $V^2$ from formula (14) may be substituted in formula (13) resulting in the formula:

$$y(r) = \frac{1}{g} \left[ \frac{\pi^2 t^2}{c^2} r_{out}^4 r - \frac{2\pi^2 t^2 r^3}{c^2} r_{out}^2 + \frac{\pi^2 t^2 r^5}{c^2} + \right. \tag{15}$$

$$\left. \frac{2\pi t r_{out}^2}{c} r\omega_{lo} - \frac{2\pi t r^3}{c} \omega_{lo} + \omega_{lo} r \right]$$

Taking the integral between $r_{in}$ and $r_{out}$ of the formula 15 results in the formula:

$$y(r) = \frac{1}{g} \int \left[ \frac{\pi^2 t^2}{c^2} r_{out}^4 \frac{r^2}{2} - \frac{2\pi^2 t^2}{c^2} \frac{r^4}{4} + \frac{\pi^2 t^2 r^6}{c^2 6} + \right. \tag{16}$$

$$\left. \frac{2\pi t}{c} r_{out}^2 \omega_{lo} \frac{r^2}{2} - \frac{2\pi t}{c} \omega_{lo} \frac{r^4}{4} + \omega_{lo}^2 \frac{r^2}{2} \right]$$

Equation (16) may be simplified as follows:

$$y(r) = \frac{1}{g} \int \left[ \frac{\pi^2 t^2}{2c^2} r_{out}^4 r^2 - \frac{\pi^2 t^2}{2c^2} r_{out}^2 r^4 + \frac{\pi^2 t^2 r^6}{6c^2} + \right. \tag{17}$$

$$\left. \frac{\pi t}{c} r_{out}^2 \omega_{lo} r^2 - \frac{2\pi t}{4c} \omega_{lo} r^4 + \frac{\omega_{lo}^2 r^2}{2} \right]$$

$$\text{where } c = \pi t \left( \frac{r_{out}^2 - r_{in}^2}{\omega_{hi} - \omega_{lo}} \right)$$

The formula (17) then may be utilized to design the surface profile 16 for any size rotor 14 where the values $r_{in}, \omega_{hi}, r_{out}$ and $\omega_{lo}$ are chosen depending upon the design factors of the feeder and the use and size of the particles for the feeder disc 14. Thus the value of y may be determined for each point on the radius of the surface 16.

Figure 3:
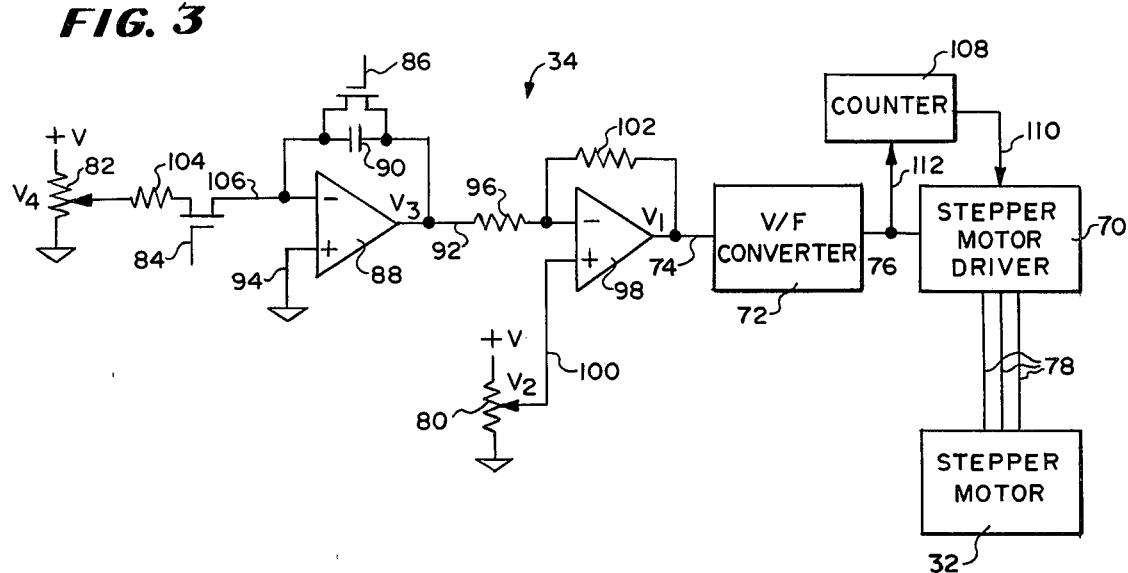
FIG. 3 is a schematic diagram of a centrifugal feeder control circuit.

Referring now to FIG. 3, one embodiment of the control 34 designed to operate the motor 32 utilizing a stepper motor is illustrated. In designing the control 34, it is desirable to have a wide adjustable range for the rotational rate of the disc 14. Further, once the initial rotation rate $\omega_{lo}$ is chosen, then the rotation rate of change or increase preferably is set to be linear at an ever increasing rate to facilitate the electronic control. The circuit 34 controls the stepper motor 32 by the rate at which pulses are applied to a conventional stepper motor driver 70 from a voltage to frequency (V/F) converter 72. The pulse rate of the converter 72 is controlled by the voltage on an input line 74. The pulses from the converter 72 are coupled to the driver 70 on a line 76. The control pulses from the stepper motor driver 70 then are coupled over a plurality of lines 78 to the stepper motor 32.

The circuit 34 includes two major controls which may be adjusted by the operator of the feeder 10. A first control potentiometer 80 is varied to set the initial speed $\omega_{lo}$ of the disc 14. A second control potentiometer 82 is adjusted to adjust the ramp or rate of speed increase of the disc 14 between $\omega_{lo}$ and $\omega_{hi}$. Both of these potentiometers are adjusted for a particular operation taking into account the design profile of the surface 16 and the physical characteristics of the particles to be expelled therefrom.

The operation of the control 34, once a batch of particles or particular material is loaded onto the surface 16, is controlled by a pair of switches 84 and 86. The switches 84 and 86 may be FET type switches and may be operated independently or in tandem. If they are operated in tandem there are three operational positions of the switches 84 and 86 which result in an "ON" ramp position, a "HOLD" ramp position and an "OFF" ramp position shown by Table 1.

TABLE 1

| Ramp or rate change | Switch 84 state | Switch 86 state |
|---|---|---|
| ON | on | off |
| HOLD | off | off |
| OFF | off | on |

In the "OFF" position the feeder 14 rotates at a constant rotational rate controlled by the initial speed control 80. The initial rotational speed of the disc 14 may be adjusted with both switches 84 and 86 in the "OFF" ramp position. When the switches are set in the "ON" ramp position the voltage on the line 74 steadily will increase as a function of time having the ramp rate set by the control 82. When the switches are set in the "HOLD" position, the voltage on the line 74 is maintained at a constant level, which allows the operator to stop the expulsion of the particles from the feeder disc 14 at any time or speed during the ramping process. With the switches in the "HOLD" position it is assumed that the particulate material will remain stationary on the surface 16 without expelling further particles from the disc 16.

Describing each of the positions in particular, in the "OFF" position the following operation occurs.

With the switch 84 off there is no input current flow to an operational amplifier 88 and the switch 86 being on shorts out a capacitor 90 providing a short circuit between the inverting input and an output line 92 of the operational amplifier 88. The non inverting input of the amplifier 88 is coupled to ground by a line 94 which will hold the output voltage on the line 92 at zero (0) volts. As a result, the line 92 essentially grounds an input resistor 96 which couples the output of the amplifier 88 to the inverting input of a second operational amplifier 98. With the resistor 96 grounded, the voltage output by the amplifier 98 on the line 74 then is determined entirely by the setting of the control 80, which is coupled by a line 100 to the non inverting input of the amplifier 98. The output voltage $V_1$ from the amplifier 98 is determined by the formula (18) where $V_2$ represents the voltage setting of the control potentiometer 80:

$$V_1 = \left( \frac{R_1}{R_2} + 1 \right) \cdot V_2 \tag{18}$$

In formula (18) $R_1$ is a resistor 102 coupled between the inverting input of amplifier 98 and the output line 74 and $R_2$ is the input resistor 96 of the amplifier 98. If $R_1$ is set equal to $R_2$, then the formula (18) reduces to:

$$V_1 = 2V_2 \tag{19}$$

In the "ON" position with switch 84 on and switch 86 off the output voltage $V_1$ of the amplifier 98 increases linearily with time. With switch 84 on the voltage set by the control potentiometer 82 is coupled through a resistor 104 on an input line 106 to the inverting input of the amplifier 88. With the switch 86 off the capacitor 90 couples the input line 106 of the amplifier 88 to the output line 92. The output voltage $V_3$ from the amplifier 88 on the line 92 then changes according to the formula (20):

$$V_3 = -\frac{V_4 t}{R_3 C} \quad (20)$$

In formula (20) $V_3$ represents the output voltage on the output line 92, $V_4$ represents the voltage set by the control potentiometer 82, $R_3$ is the resistor 104, c is the capacitor 90 and t is the time in seconds. The formula for the voltage $V_1$ on the output line 74 then becomes:

$$V_1 = \left(\frac{R_1}{R_2} + 1\right) \cdot V_2 - \frac{R_1}{R_2} \cdot V_3 \quad (21)$$

$$= \left(\frac{R_1}{R_2} + 1\right) V_2 + \frac{R_1}{R_2} \cdot \frac{V_4 t}{R_3 C}$$

If $R_1$ is set equal to $R_2$ then formula (21) reduces to:

$$V_1 = 2V_2 + \frac{V_4 t}{R_3 C} \quad (22)$$

It can be seen from the formula (22) that the voltage change in $V_1$ adds to the voltage set by the initial speed control 80. Typical values for the elements utilizing a stepper motor 32 are 12 megohms for resistor 104, 5 microfarads for capacitor 90 and 10,000 ohms for both resistors 96 and 102. The amplifiers 88 and 98 may be standard operational amplifiers and the voltage to frequency converter 72 preferably has a wide dynamic range.

In the "HOLD" position, the switch 84 is off preventing current from being applied to the inverting input of amplifier 88 through resistor 104. The switch 86 is off allowing the capacitor 90 to act in the circuit of the amplifier 88. The formula for $V_1$ in the "HOLD" position is:

$$V_1 = 2V_2 + \frac{V_4 t_1}{R_3 C} \quad (23)$$

Equation (23) assumes that $R_1$ is equal to $R_2$, with $t_1$ being the time elapsed between the setting of the switches in the "ON" position and resetting them to the "HOLD" position. The capacitor C will hold the last value of $V_3$ attained at the time the "HOLD" position is initiated.

The above formula and operation generally perform as desired; however, for particles which are not regular such as angular, acircular or needle-shaped particles, friction between the particles and the surface 16 of the rotor 14 may become significant. To overcome this friction the stepper motor may be jogged at a predetermined frequency of pulses, which may be obtained by a counter 108 coupled to the stepper motor driver 70 by a line 110 and to the pulse input line 76 of the stepper motor driver by a line 112. The counter may count the pulses on the input line 76 and following a predetermined number or frequency of pulses provide a reverse pulse on the line 110. The reverse pulse will cause the stepper motor driver 70 to generate a reverse pulse to the stepper motor 32 which will jog, or momentarily reverse the stepper motor 32 to overcome the hysteresis resistant between the particles and the surface 16. The surface 16 may be formed integral with the rest of the rotor 14 or may be a separate slick surface of plastic or other type material, but the hysteresis friction is not completely overcome by the smoothness or slickness of the surface 16. The particles which are irregular and may become adhered to the surface in a fixed position, will be expelled at the desired control rate by reversing the motor. Again, as mentioned before this is not a problem for regularly shaped particles.

Figure 4:
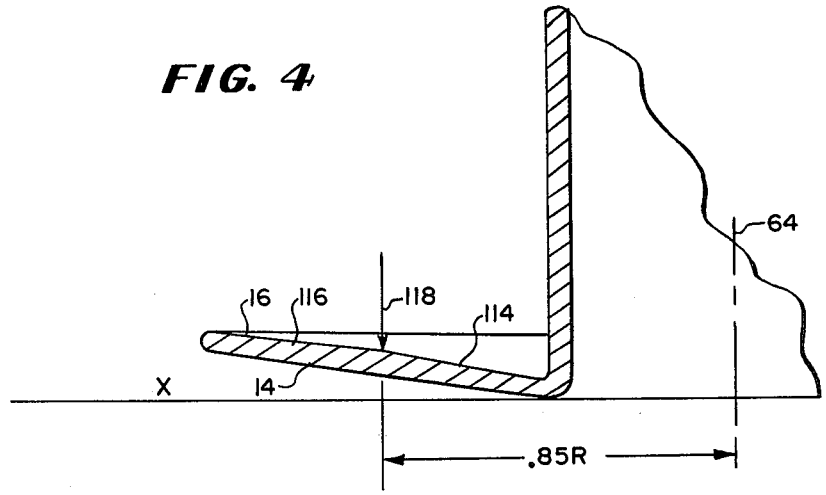
FIG. 4 is an enlarged partial side sectional view of a second embodiment of a feeder disc of the centrifugal feeder.

Referring now to FIG. 4, one embodiment of the rotor disc 14 is illustrated which is an approximation of the curve determined by the formula (17). In this approximation, the curve actually is formed or machined into a molded or otherwise formed material on the surface 16 in the form of a first straight line segment 114 and a second straight line segment 116. The two segments are at a different angles with the horizontal axis x and may be blended together at a point 118. In the example shown, the point 118 is 0.85 of the total radius of the disc 14. As stated above, the straight line segments may be molded, machined or otherwise formed in the surface 16.

A convenient method of determining the straight line approximation shown in FIG. 4, is to plot the values of y for the disc 14 from the formula (17) and then fit the two lines to the resulting curve. The disc 14 also may have a single straight line conical surface 16 or other shape with the acceleration being varied between $\omega_{lo}$ and $\omega_{hi}$ to achieve the desired particle discharge rate.

The above analysis of the surface 16 was performed with an assumed essentially monolayer of particles spread around the entire surface 16 of the disc 14. Even if the particular material is heaped on one portion of the surface 16, when the rotor 14 is rotated the particular material will spread out to have at least a monolayer at the outer edge or rim 58 of the surface 16. Also, as described before $\omega_{lo}$ and $\omega_{hi}$ are chosen such that at $\omega_{lo}$ the first particles will start being expelled from the rim 58 with the last particles being expelled by or at the speed $\omega_{hi}$. The key to expelling the particles at the desired rate is to accelerate at a slow rate of change between $\omega_{lo}$ and $\omega_{hi}$. The particles are expelled essentially by centrifugal force, with the "jog" applied if necessary. The viscosity of the fluid or air in which the disc 14 is rotated has been ignored. It has been found to be essentially negligible if the body wall 20 is circular since most of the fluid will rotate with the rotor, because of the shear forces associated with the viscosity of the fluid. For air or other light gases the effect is negligible.

As described, the initial discharge speed $\omega_{lo}$ can be selected, as well as the final discharge speed $\omega_{hi}$ as well as the discharge rate between the two speeds. In the example given, a uniform volume per unit of time dischargge rate is chosen but an increasing or decreasing discharge rate of particles also could be chosen if desired. Further, although the stepper motor 32 is convenient a DC torque motor with feedback having the necessary control also may be utilized. The theoretical limits to the low and high discharge speeds ($\omega_{lo}$ and $\omega_{hi}$) are not limited; however, utilizing the stepper motor 32 it is preferable to set the speeds in the smooth operational range of the motor. This may be between 50 and 250 rpm, because below 50 rpm the operation of the motor is not smooth and above 250 rpm the motor may not be able to follow the drive pulses and may stop.

The type of particles is not critical; however, very fine particles may float in the fluid 18 and therefore it might be preferable to have the fluid intake 52 above the level of the rotor surface 16 so that the downward movement of the fluid 18 through the port 60 will sweep the particles along with it. If the particles are sufficiently dense, the problem does not occur. The feed rate of the particles from the disc rim 58 theoretically is independent of size and density of particles, the viscosity of the surrounding fluid and to at least some extent the particle shape. The feeder 10 does not inherently separate by particle size, but some segregation of particles by size will take place in the centrifugal force field when the disc is rotating. Referring to FIG. 2, it also would be possible to ramp up to the initial speed at a very high rate of change of speed and then have a second lower ramp once $\omega_{lo}$ is reached. The initial speed $\omega_{lo}$ utilizing a DC motor could be very close to zero (0) rpm.

Many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A method of operating a centrifugal feeder having a substantially cylindrical feeder disc of generally conical configuration with an upwardly inclined generally concave surface symmetrical about a vertical axis comprising the steps of:
   feeding an amount of particulate material onto the feeder disc surface,
   rotating said disc at a first angular velocity at which particles are expelled from the disc surface, and
   rotating said disc through at least one other angular velocity at which particles are expelled from the disc surface,
wherein the first angular velocity is not capable of causing the expulsion of the particles expelled at the least one other angular velocity.

2. A method as claimed in claim 1 in which the change from said first angular velocity to said least one other angular velocity is at a linear rate.

3. A method as claimed in claim 1 in which the change from said first angular velocity to said least one other angular velocity is at a non-linear rate.

4. A method as claimed in claim 1 including the step of:
   momentarily reversing the disc rotation at a predetermined frequency before the step of roating said disc through at least one other angular velocity,
whereby the friction of the particles on the disc surface is overcome.

5. A method as claimed in claim 1 in which said step of rotating said disc at said first angular velocity is performed at an accelerated increased rate of speed until reaching a first predesigned initial particle explusion angular velocity.

6. A method as claimed in claim 5 in which said disc is rotated from said first angular velocity to said least one other angular velocity so as to expel all of said particles from said disc surface.

7. A method as claimed in claim 1 in which said step of rotating said disc at said first angular velocity is performed at a high rate of speed to reach said first expulsion velocity.

8. A method as claimed in claim 7 in which said disc is rotated from said first angular velocity to said least one other angular velocity at a controlled change of speed rate.

9. The method as claimed in claim 1 wherein said upwardly inclined generally concave surface of said feeder disc includes a curvature defining at least one equalibrium point, whereby particles disposed beyond said point are expelled from the disc surface and particles disposed within said point remain on the disc surface at one given angular velocity.

10. A centrifugal feeder having a substantially cylindrical feeder disc of generally conical configuration with an upwardly inclined generally concave surface symmetrical about a vertical axis adapted to feed particles from said surface comprising,
    means for rotating said disc at a first angular velocity at which particles are expelled from the disc surface, and
    means for rotating said disc through at least one other angular velocity at which particles are expelled from the disc surface,
wherein the first angular velocity is not capable of causing the expulsion of the particles expelled at the least one other angular velocity.

11. A feeder as claimed in claim 10 including means for changing the rotation of said disc from the first angular velocity to the least one other angular velocity at a linear rate.

12. A feeder as claimed in claim 10 including means for changing the rotation of said disc from the first angular velocity to the least one other angular velocity at a non-linear rate.

13. A feeder as claimed in claim 10 including means for changing the rotation of said disc from the first angular velocity to the least one other angular velocity, and means for inhibiting said changing means to hold said one other angular velocity substantially constant.

14. A feeder as claimed in claim 10 including means for momentarily reversing the disc rotation at the first angular velocity at a predetermined frequency to overcome hysteresis friction on the disc surface.

15. A feeder as claimed in claim 10 in which said means for rotating said disc at the first angular velocity does so at an increased rate of speed until reaching the first predesigned initial particle expulsion speed.

16. A feeder as claimed in claim 15 including means for changing the rotation of said disc from the first angular velocity to the least one other angular velocity at a controlled change of speed rate.

17. A feeder as claimed in claim 10 in which said disc has a shape adapted to expel particles at said first angular velocity, and means for accelerating said disc at a high rate to reach said first angular velocity.

18. A feeder as claimed in claim 17 in which said disc has a shape adapted to expel the last particles on the disc surface, and means for changing the rotation of said disc from the first angular velocity to the least one other angular velocity at a controlled change of speed rate.

19. The centrifugal feeder as claimed in claim 10 wherein said upwardly inclined generally concave surface of said feeder disc includes a curvature defining at least one equalibrium point, whereby particles disposed beyond said points are expelled from the disc surface and particles disposed within said point remain on the disc surface at one given angular velocity.

* * * * *